(12) United States Patent
Hirsh (10) Patent No.: US 7,761,141 B2
(45) Date of Patent: Jul. 20, 2010

(54) NON-INVASIVE METHOD AND DEVICE TO MONITOR CARDIAC PARAMETERS WITHOUT USE OF ELECTRICAL-MECHANICAL INTERVAL

(76) Inventor: Robert Hirsh, 208 Sycamore Ave., Merion Station, PA (US) 19066

( * ) Notice: Subject to any disclaimer, the term of this patent is extended or adjusted under 35 U.S.C. 154(b) by 755 days.

(21) Appl. No.: 11/689,934

(22) Filed: Mar. 22, 2007

(65) Prior Publication Data
US 2007/0191724 A1 Aug. 16, 2007

Related U.S. Application Data

(60) Continuation-in-part of application No. 11/266,122, filed on Nov. 3, 2005, now Pat. No. 7,657,306, which is a division of application No. 09/999,125, filed on Oct. 31, 2001, now Pat. No. 7,054,679.

(51) Int. Cl.
*A61B 5/029* (2006.01)
(52) U.S. Cl. .................. 600/513; 600/485; 600/508; 600/526
(58) Field of Classification Search .................. None
See application file for complete search history.

(56) References Cited

U.S. PATENT DOCUMENTS

| | | | |
|---|---|---|---|
| 4,203,451 A | 5/1980 | Panico |
| 4,677,984 A | 7/1987 | Sramek |
| 5,103,828 A | 4/1992 | Sramek |
| 5,181,517 A | 1/1993 | Hickey |
| 5,211,177 A | 5/1993 | Chesney et al. |
| 5,309,917 A | 5/1994 | Wang et al. |
| 5,368,040 A | 11/1994 | Carney |
| 5,497,778 A | 3/1996 | Hon |
| 6,090,047 A | 7/2000 | Kass et al. |
| 6,440,078 B1 | 8/2002 | Curiel et al. |

(Continued)

FOREIGN PATENT DOCUMENTS

WO 92/06633 4/1992

(Continued)

OTHER PUBLICATIONS

European Patent Office Extended Search Report dated Jun. 20, 2008 for corresponding EP 08100922.7.

(Continued)

*Primary Examiner*—Kennedy J Schaetzle
(74) *Attorney, Agent, or Firm*—Knoble Yoshida & Dunleavy, LLC (57) ABSTRACT

A method of and a device for non-invasively measuring the hemodynamic state of a subject or a human patient involve steps and units of non-invasively or minimally invasively measuring cardiac cycle period, mean arterial pressure, stroke volume, diastolic interval and ejection interval and converting the measured mean arterial pressure, stroke volume, diastolic interval and ejection interval into the cardiac parameters such as Preload, Afterload and Contractility, which are the common cardiac parameters used by an anesthesiologist. In the current invention, the use of electrical-mechanical interval has been eliminated for various advantageous reasons. The converted hemodynamic state of a patient is displayed on a screen as a three-dimensional vector with each of its three coordinates respectively representing Preload, Afterload and Contractility. Therefore, a medical practitioner looks at the screen and—quickly obtains the important and necessary information.

61 Claims, 4 Drawing Sheets

U.S. PATENT DOCUMENTS

| | | |
|---|---|---|
| 6,939,303 B2 | 9/2005 | Curiel |
| 6,994,675 B2 | 2/2006 | Sharrock |
| 7,054,679 B2 | 5/2006 | Hirsh |
| 2006/0167363 A1 | 7/2006 | Osypka et al. |

FOREIGN PATENT DOCUMENTS

| | | |
|---|---|---|
| WO | 92/11805 | 7/1992 |

OTHER PUBLICATIONS

Christine Berton and Bernard Cholley: "Equipment review: New techniques for cardiac output measurement oesophageal Doppler, Fick principle using carbon dioxide, and pulse contour analysis", Critical Care, Biomed Central Ltd., London, GB, vol. 6., No. 3, Apr. 25, 2002, pp. 216-221.

Hett D. A. et al., "Non-invasive cardiac output monitoring", Current Anaesthesia and Critical Care, Churchill Livingstone, London, GB, vol. 14, No. 4, Aug. 1, 2003, pp. 187-191.

Nakagaware et al., "A portable instrument for non-invasive monitoring of beat-by-beat cardiovascular haemodynamic parameters based on the volume-compensation and electrical-admittance method", Medical and Biological Engineering and Computing, vol. 38, No. 1, Jan. 2000, pp. 17-25.

Muchada et al., "Non-invasive monitoring of hemodynamic profile during general anesthesia",Minerva anestesiologica, Italy, Jun. 1990, vol. 56, No. 6, pp. 199-205,Database Medline [online], abstract only.

Sramek, B.B., "Physiologic Chart for Rapid Identification of Causes of Abnormal Haemodynamics", Annals of the Academy of Medicine, vol. 23, No. 6, Nov. 1,1994, pp. 26-32.

Huemer, et al., "Influence of Positive End-Expiratory Pressure on Right and Left Ventricular Performance Assessed by Doppler Two-Dimensional Echocardiography", Chest, vol. 106, No. 1, Jul. 1004, pp. 67-73.

Harada et al., "Principle of a noninvasive method of measuring maximum pressure change with respect to time of the left ventricle theory and experiments", Heart and Vessels, vol. 3, No. 1, 1987, pp. 25-32.

Campbell et al., "A comparison of cardiac rate-pressure product and pressure-rate quotient with Holter monitoring in patients with hypertension and cardiovascular disease: a follow-up report" Oral Surgery, Oral Medicine, Oral Pathology, Oral Radiology and Endodontics, vol. 84, No. 2, Aug. 1997, pp. 125-128.

Adler et al., "Time to dp/dt/sub/max reflects both intropic and chronotropic properties of cardiac contraction: a conscious dog study", Physiological Measurement, Nov. 1996, vol. 17, No. 4, pp. 287-295.

Welham et al., The First Derivative of the Transthoracic Electrical Impedance as an Index of Changes in Myocardial Contractility in the Intact Anaesthetized Dog Intensive Care Medicine, vol. 4, No. 1, Jan. 1978, p. 43-50.

Klein, G., M.D., Emmerich, M., M.D., Clinical Evaluation of Noninvasive Monitoring Aortic Blood Flow, (ABF) by a Transesophageal Echo-Doppler-Device; Anesthesiology 1998; V89 No. 3A: A953.

Wallace, A.W., M.D., PhD, et al., Endothracheal Cardiac output Monitor; Anesthesiology 2000;V92; pp. 178-189.

Braunwald, E. M.D., ed., Heart Disease, A Textbook of Cardiovascular Medicine; Fourth Edition; Philadelphia, W.B. Saunders Company; 1992; p. 420.

Braunwald, E. M.D., ed., Heart Disease, A Textbook of Cardiovascular Medicine; Fourth Edition; Philadelphia, W.B. Saunders Company; 1992; p. 431.

Connors, A.F. Jr., M.D.,et al.; The Effectiveness of Right Heart Catherization in the Initial Care of the Critically Ill Patients; J. Amer. Med. Assn., 1996; 276:889-897.

Dalen, J.E. Bone R.C.: Is It Time to Pull the Pulmonary Catheter? J. Amer. Med. Assn., 1996; 276:916-918.

English Translation of JP Office Action dated Dec. 12, 2008 for related JP Application No. 2003-539529.

Yoshizawa et al., "A Noninvasive Estimation Tool for Cardiac Function (Emax PVA)", Anthology of papers regarding Bionics and Physiology Symposium, Japan, Oct. 13, 2000, 15th, pp. 189-192.

NON-INVASIVE METHOD AND DEVICE TO MONITOR CARDIAC PARAMETERS WITHOUT USE OF ELECTRICAL-MECHANICAL INTERVAL

CROSS REFERENCE TO RELATED APPLICATION

This is a continuation-in-part application of the application Ser. No. 11/266,122 filed on Nov. 3, 2005, and issued as U.S. Pat. No. 7,657,306 on Feb. 2, 2010, which is a divisional application of the application Ser. No. 09/999,125 filed on Oct. 31, 2001 and issued as U.S. Pat. No. 7,054,679 on May 30, 2006.

BACKGROUND OF THE INVENTION

1. Field of the Invention

The present invention relates to an alternative non-invasive method and device to monitor cardiac parameters.

2. Description of the Prior Art

U.S. Pat. No. 7,054,679, NON-INVASIVE METHOD AND DEVICE TO MONITOR CARDIAC PARAMETERS issued to Hirsh in 2001, describes a vector space, whose basis vectors are non-invasively obtained in a substantially easy manner. In particular, the vector space $$N=\{T, MAP, EI, DI, E-M\}$$

is described, where T is the Cardiac Period, MAP is the Mean Arterial Pressure in a peripheral artery, preferably the Radial Artery, and E-M is the Electrical-Mechanical Interval. In one embodiment, the E-M interval is measured as the time interval between a signal electrical event in the EKG and a concomitant, causally related mechanical event in the peripheral (radial arterial) pulse wave. EI is the Ejection Interval, the time interval between the opening and the closing of the Aortic Valve. DI is the Diastolic Interval, the time interval between the opening and the closing of the mitral valve.

In one preferred embodiment, the electrical event is measured as the time of the peak in the amplitude of the second derivative of the EKG such as in Einthoven's Lead II. This corresponds roughly to the Q-wave trough in the EKG, which in Lead II has a negative-going depolarization. It is the time at which the EKG depolarization voltage is accelerating maximally upwards. Call this event $T_E$.

In one preferred embodiment, the mechanical event is the time of the peak in the value of the second derivative of the arterial pressure wave. This is the instant in time at which the pressure wave is accelerating maximally upwards. It corresponds roughly to the time at which the arterial pressure wave starts to take off from its lowest value at the beginning of systole. Call this event $T_M$ The Electrical-Mechanical Interval, $$E-M = T_M - T_E \qquad \text{eq. 1}$$

This E-M interval has many interesting properties. For example, it can be used to predict the contractile state of the myocardium. If the contractility of the myocardium is described by the quantity $dP/dt_{max}$, which is the maximum value of the first derivative of Left Ventricular Pressure as denoted by P during systole, we can say that $$\ln(dP/dt_{max}) = k(1/E-M) + c \qquad \text{eq. 2}$$

where 'k' and 'c' are constants of proportionality. The natural log of $dP/dt_{max}$ is linearly proportional to $1/(E-M)$. This is taught by U.S. Pat. No. 7,054,679.

Similarly, there exists a set of transformation functions, which operate on the quantities contained in N. U.S. Pat. No. 7,054,679 teaches some, preferred embodiments of such functions. Those functions of N in turn, represent a new set of quantities, also expressed as a vector, in a new vector space I. The set of quantities in the vector I have the extremely useful property that they linearly track with the set of hemodynamic quantities that are historically and conventionally obtained only in invasive manners at considerable expense and risk to the patient. These hemodynamic quantities include {Preload, Afterload, Contractility, Stroke Volume, Cardiac Output, End-Diastolic Left Ventricular Myocardial Compliance}.

Using the formalisms of Linear Algebra, we can place appropriately constructed transformation functions into an appropriately constructed diagonal matrix and use that matrix to operate on the vector in N to obtain a vector in I. Significantly, any possible hemodynamic state is described uniquely by exactly one point in N. We can say that N 'spans' cardiovascular space. Every point in N is mathematically mapped on to exactly one point in I. There exist no unmapped points in N. The mathematical mapping is 'one-to-one', as well as 'onto'. Likewise, any possible hemodynamic state is described by exactly one point in I.

Moreover, U.S. Pat. No. 7,054,679 teaches that it is possible to display the quantity {Preload, Afterload, Contractility} which is approximated by

{Left Ventricular End-Diastolic Pressure, Systemic Vascular Resistance, $dP/dt_{max}$} as a vector in a three dimensional Cartesian space in real time to be displayed on a computer screen. Each of the three quantities is represented as a component vector along one of three mutually perpendicular axes. This is done simply by using the appropriate mathematical transforms on the appropriate non-invasive quantities in N, as in U.S. Pat. No. 7,054,679. Such a real-time, noninvasive display is very empowering to clinicians and allows even inexperienced clinicians to visualize and to understand hemodynamic and physiological states of their patients as they undergo surgery or as their disease process evolves through time. It can empower healthcare workers to deliver better care at lower cost with considerably less risk to the patient.

A problem with the non-invasive hemodynamic monitoring approach described in the above has to do with the nature of the E-M interval. While the relation between the E-M interval and the ratio between Stroke Volume and the Ejection Interval (SV/EI) is practically invariant over logarithmic ranges of Systemic Vascular Resistance (SVR) and Left Ventricular End-Diastolic Pressure (LVEDP), the E-M interval is difficult to standardize. If the anatomical position of the arterial pressure detector is controlled for, say by placing it at the radial artery, there remains the problem of normalizing the E-M by the patient's height, arm-span, or some other feature of the patient's physiognomy. While this can be easily accomplished, there also remains the problem of correcting the E-M for 1) the effects of a decrease in the speed of signal transduction by the Purkinje fibers in the cardiac conduction system and the myocardium itself with increasing age, and 2) the decrease in the elasticity of the artery as the patient ages, or as a consequence of illness, and its shortening effect on the time of flight of the pulse wave from the aortic valve to the pressure detector.

The above described problems necessitate the development of a nomogram based on factors such as height, and age, and the presence of disease that might be used to predict the coefficients and constants of linear proportionality (k, c). Furthermore, a nomogram is used for calibration of the various relations described in U.S. Pat. No. 7,054,679 such as $$\exp(1/E\text{-}M) = k(SV/EI) + c \qquad \text{eq. 3}$$

Such a nomogram would be based on studies of large populations of patients. It could be used within reasonable limits of statistical probability. Alternatively, some other well-accepted invasive or minimally invasive method could be used to calibrate the system for each individual patient on a one-time basis to establish a base line. Unfortunately, these procedures may need to be performed while the patient is under anesthesia or deep sedation. The utility of said calibration could persist for months to years, barring some significant evolution in the natural history of the patient's disease.

Since U.S. Pat. No. 7,054,679 was conceived, three new technologies have emerged that allow for the non-invasive measurement of the Ejection Interval (EI) during Systole and of the Stroke Volume. The first is Esophageal Doppler technology such as the Hemosonic 100 or the Deltex device. The Hemosonic 100 uses an esophageal Doppler and A-mode ultrasound to measure the diameter of the descending aorta as a function of time as the pulse wave traverses it and then integrates the cross-sectional area of the descending Aorta times the cross sectional blood velocity over the ejection interval to yield the stroke volume (SV). The Deltex device simply measures the average blood flow in the descending Aorta and yields a 'stroke distance' over the ejection interval that does not correct for variations in the cross sectional area of the aorta.

The second is Pulse Contour technology, which approximates the (SV) from the peripheral arterial pulse pressure that is measured invasively using an indwelling arterial catheter. In principle, the Pulse Contour method can be used with the trace of the non-invasively measured pulse wave, using the T-line from Tensysmedical. One example of pulse contour technology is the Edwards Vigilio System, and LiDCO, which is an indwelling Lithium ion electrode used to calibrate the system with cardiac output information. Another is the Pulsion PiCCO system by Phillips.

The third is Impedance Cardiography technology. This technology injects a high frequency, low milliamp current into the chest from two or more skin electrodes. Two or more skin electrodes are used immediately inside the current-injecting electrodes. A voltage is measured across these sensing electrodes, and impedance is calculated as it varies with the cardiac cycle in a complex way. Stroke Volume and Ejection Interval are also calculated from the waveform based upon proprietary algorithms on a beat-to-beat basis. Examples include the IQ AOE Impedance Cardiography System, and the Physioflow device.

A second problem with the E-M interval as derived from the EKG signal and the peripheral arterial pressure wave is that the beat-to-beat measurement of the arterial pressure wave has required the use of an invasive indwelling peripheral arterial catheter. Although the use of such a catheter is routine, it has been associated with patient injury including rare but catastrophic loss of a patient's hand. Another technology, which has emerged since 2001 and already alluded to, is the T-line by Tensysmedical, which obviates the above problem. This device gives the clinician a non-invasively obtained radial arterial pressure wave that is the physiological equivalent of an invasive arterial pressure wave signal. It works by the use of a piezo-resistive element configured in a Wheatstone bridge circuit. The piezo-resistive element is held over the radial artery by means of a spring loaded clamp. A first servomotor then moves the piezo-resistive element over the width of the ventral side of the wrist in the 'x' direction to find the maximum amplitude of the radial arterial pulse. A second servomotor moves the piezo-resistive element vertically in the 'z' direction bringing a servo-controlled pressure to bear upon the circular cross section of the radial artery. It adjusts itself in the 'z' direction until it gets a maximal amplitude of the pressure indicative of the mean arterial pressure inside the radial artery. Sinusoidal deviations from this pressure during the pulse wave are displayed as a pressure wave on a suitable display. By using this device in conjunction with an EKG signal, it is possible to create a physiologically useful E-M interval as described in U.S. Pat. No. 7,054,679, and the E-M interval stands in a physiologically useful relation to $dP/dt_{max}$ and SV/EI.

These new technologies put a real time beat-to-beat data stream of EI and SV easily within the grasp of clinicians. They do not depend on the time-honored methods of thermodilution using a Swan-Ganz catheter and thereby avoid the level of trespass and risk of injury associated with this device.

SUMMARY OF THE INVENTION

The present invention frames an alternative noninvasive vector space, N' consisting of hemodynamic quantities that are easily measured in a non-invasive manner, without requiring the measurement of the E-M interval. The present invention circumvents the problem of standardizing the E-M interval in a way that enables clinicians to easily make comparisons between the non-invasive hemodynamic parameters of one patient with that of another. This alternative vector space is denoted by $$N' = \{T, DI, EI, MAP, SV\},$$

where T is the cardiac period measured from the peak of one R-wave on an EKG to the peak of the next R-wave, DI is the diastolic filling interval from the opening to the closing of the mitral valve, EI is the Ejection Interval from the opening to the closing of the aortic valve, MAP is the Mean Arterial Pressure in a peripheral artery such as the radial artery at the wrist, and SV is the Stroke Volume.

The invention is based upon the idea that there exists a set of functions to describe the behavior of one or more variables contained in the vector space N'. Each function is monotonically increasing with respect to a cardiac function parameter such as $\{LVEDP, SVR, dP/dt_{max}\}$, in a clinically useful, and predictable way. In this regard, appropriately modified functions are placed into the form of a diagonal matrix which operates on N' to yield a vector in the invasive vector space I. Cartesian space has three mutually perpendicular axes such as $\{LVEDP, SVR, dP/dt_{max}\}$, or some similar, clinically useful approximation to {Preload, Afterload, Contractility}. A vector in this space is displayed on a computer screen, with suitable indices of Stroke Volume and Cardiac Output to inform the clinician about changes in the hemodynamic state of the patient on a beat-to-beat or breath-by-breath basis so as to empower him or her to titrate fluid therapy and vasoactive agent therapy in a physiologic and parameter-specific fashion.

According to the first aspect of the current invention, a method of monitoring cardiac parameters includes the steps of calibrating a stroke volume as denoted by SV and mean arterial pressure as denoted by MAP in a minimally invasive manner; non-invasively measuring from a subject a plurality of predetermined non-invasive cardiac parameters including the MAP, the SV, a cardiac period as denoted by T, a diastolic filling interval from the opening to the closing of the mitral valve as denoted by DI and an ejection interval as denoted by EI; converting the non-invasive cardiac parameters into a plurality of invasive cardiac analogues including preload as denoted by P, afterload as denoted by A and contractility as denoted by C in a monotonically increasing one-to-one and onto manner; and displaying a vector indicating a hemodynamic state.

According to the second aspect of the current invention, a system for monitoring cardiac parameters includes a calibration unit for calibrating a stroke volume as denoted by SV and mean arterial pressure as denoted by MAP in a minimally invasive manner; a non-invasive cardiac parameter measuring unit connected to the calibration unit for non-invasively measuring from a subject a plurality of predetermined non-invasive cardiac parameters including the SV, the MAP, a cardiac period as denoted by T, a diastolic filling interval from the opening to the closing of the mitral valve as denoted by DI and an ejection interval as denoted by EI; a conversion unit connected to the non-invasive cardiac parameter measuring unit for converting the non-invasive cardiac parameters into a plurality of invasive cardiac analogues including preload as denoted by P, afterload as denoted by A and contractility as denoted by C in a monotonically increasing one-to-one and onto manner; and a display unit connected to the conversion unit for displaying a vector indicative of a hemodynamic state.

According to the third aspect of the current invention, a method of monitoring cardiac parameters includes the steps of measuring in a substantially non-invasive manner from a subject a plurality of predetermined non-invasive cardiac parameters including a stroke volume as denoted by SV, mean arterial pressure as denoted by MAP, a cardiac period as denoted by T, a diastolic filling interval from the opening to the closing of the mitral valve as denoted by DI and an ejection interval as denoted by EI; converting the non-invasive cardiac parameters into a plurality of invasive cardiac analogues including preload as denoted by P, afterload as denoted by A and contractility as denoted by C in a monotonically increasing one-to-one and onto manner; and displaying a vector indicating a hemodynamic state.

According to the fourth aspect of the current invention, a system for monitoring cardiac parameters includes a non-invasive cardiac parameter measuring unit for measuring in a substantially non-invasive manner from a subject a plurality of predetermined non-invasive cardiac parameters including a stroke volume as denoted by SV, mean arterial pressure as denoted by MAP, a cardiac period as denoted by T, a diastolic filling interval from the opening to the closing of the mitral valve as denoted by DI and an ejection interval as denoted by EI; a conversion unit connected to the non-invasive cardiac parameter measuring unit for converting the non-invasive cardiac parameters into a plurality of invasive cardiac analogues including preload as denoted by P, afterload as denoted by A and contractility as denoted by C based in a monotonically increasing one-to-one and onto manner; and a display unit connected to the conversion unit for displaying a vector indicative of a hemodynamic state.

According to the fifth aspect of the current invention, a method of evaluating a patient based upon non-invasively measured parameters of myocardial contractility includes the steps of measuring in a substantially non-invasive manner from the patient a plurality of predetermined non-invasive cardiac parameters including a stroke volume as denoted by SV and an ejection interval as denoted by EI at rest and under duress; and equating one of SV/EI and ln(SV/EI) to the myocardial contractility.

According to the sixth aspect of the current invention, a system for making pre-anesthetic assessment of a patient based upon measure of myocardial contractility includes a cardiac parameter measuring unit for measuring in a substantially non-invasive manner from the patient a plurality of predetermined non-invasive cardiac parameters including a stroke volume as denoted by SV and an ejection interval as denoted by EI; and a determination unit connected to the non-invasive cardiac parameter measuring unit for equating one of SV/EI and ln(SV/EI) to myocardial contractility.

According to the seventh aspect of the current invention, a method of detecting myocardial ischemia in a patient based upon non-invasively measured parameters includes the steps of calibrating a stroke volume as denoted by SV and mean arterial pressure as denoted by MAP in a minimally invasive manner for the patient; non- invasively measuring from the patient a plurality of predetermined non-invasive cardiac parameters including the MAP, the SV, a cardiac period as denoted by T, a diastolic filling interval from the opening to the closing of the mitral valve as denoted by DI and an ejection interval as denoted by EI; approximating the rate of change in volume with respect to the rate of change in pressure in the left ventricle (dV/dP) by the change in LV volume divided by the change in LV pressure during diastolic filling ($\Delta V/\Delta P$); evaluating the $\Delta V/\Delta P$ by the non-invasively measured cardiac parameters; and detecting ischemia in the patient based upon the evaluated $\Delta V/\Delta P$.

According to the eighth aspect of the current invention, a system for detecting myocardial ischemia in a patient based upon non-invasively measured parameters includes a calibration unit for calibrating a stroke volume as denoted by SV and mean arterial pressure as denoted by MAP in a minimally invasive manner for the patient; a non-invasively measuring unit connected to the calibration unit for non-invasively measuring from the patient a plurality of predetermined non-invasive cardiac parameters including the MAP, the SV, a cardiac period as denoted by T, a diastolic filling interval from the opening to the closing of the mitral valve as denoted by DI and an ejection interval as denoted by EI; and a determination unit connected to the non-invasively measuring unit for approximating the rate of change in volume with respect to the rate of change in pressure in the left ventricle (dV/dP) by the change in LV volume divided by the change in LV pressure during diastolic filling ($\Delta V/\Delta P$) to evaluating the $\Delta V/\Delta P$ by the non-invasively measured cardiac parameters, said determination unit detecting ischemia in the patient based upon the evaluated $\Delta V/\Delta P$.

According to the ninth aspect of the current invention, a method of quantifying a subject's ability to effect perfusion homeostasis through the physiologic modulation of myocardial contractility includes the steps of measuring beat-to-beat SV/EI data over time in a substantially non-invasive manner; obtaining a running average of the beat-to-beat SV/EI data, where the number of beats in the running average equals the number of beats in one respiratory cycle or at least two consecutive respiratory cycles; determining variations in the SV/EI data with respect to the running averaged SV/EI data; determining an average of the variations and a standard deviation of the variations to generate a contractile function metric; and determining based upon the contractile function metric as to whether or not the subject experiences myocardial contractile decompensation.

According to the tenth aspect of the current invention, a system for quantifying a subject's ability to effect perfusion homeostasis through the physiologic modulation of myocardial contractility includes a measuring unit for measuring beat-to-beat SV/EI data over time in a substantially non-invasive manner; a determination unit connected to the measuring unit obtaining a running average of the beat-to-beat SV/EI data, where the number of beats in the running average equals the number of beats in one respiratory cycle or at least two consecutive respiratory cycles, the determination unit determining variations in the SV/EI data with respect to the running averaged SV/EI data and an average of the variations and a standard deviation of the variations to generate a contractile function metric; and a display unit connected to the determination unit for displaying the contractile function metric for determining whether or not the subject experiences myocardial contractile decompensation.

According to the eleventh aspect of the current invention, a method of monitoring cardiac parameters includes the steps of calibrating a stroke volume as denoted by SV and mean arterial pressure as denoted by MAP in a minimally invasive manner; non-invasively measuring from a subject a plurality of predetermined non-invasive cardiac parameters including the MAP, the SV, a cardiac period as denoted by T, a diastolic filling interval from the opening to the closing of the mitral valve as denoted by DI and an ejection interval as denoted by EI; converting the non-invasive cardiac parameters into a plurality of invasive cardiac analogues including preload as denoted by P, afterload as denoted by A and contractility as denoted by C in a monotonically increasing one-to-one and onto manner, $C \propto \ln(SV/EI)$, wherein SV is obtained in a non-invasive manner; and displaying a vector indicating a hemodynamic state.

According to the twelfth aspect of the current invention, a system for monitoring cardiac parameters includes a calibration unit for calibrating a stroke volume as denoted by SV and mean arterial pressure as denoted by MAP in a minimally invasive manner; a non-invasive cardiac parameter measuring unit connected to the calibration unit for non-invasively measuring from a subject a plurality of predetermined non-invasive cardiac parameters including the SV, the MAP, a cardiac period as denoted by T, a diastolic filling interval from the opening to the closing of the mitral valve as denoted by DI and an ejection interval as denoted by EI; a conversion unit connected to the non-invasive cardiac parameter measuring unit for converting the non-invasive cardiac parameters into a plurality of invasive cardiac analogues including preload as denoted by P, afterload as denoted by A and contractility as denoted by C in a monotonically increasing one-to-one and onto manner, $C \propto \ln(SV/EI)$, wherein SV is obtained in a non-invasive manner; and a display unit connected to the conversion unit for displaying a vector indicative of a hemodynamic state.

DETAILED DESCRIPTION OF THE PREFERRED EMBODIMENTS

The disclosure of U.S. Pat. No. 7,054,679, which is a parent case, has been incorporated herein by external reference.

Equations 2 and 3 are empirical relations. Expressing equations (eqs.) 2 and 3 as a linear proportionality, we have $$\ln(dP/dt_{max}) \alpha\, 1/(E-M) \qquad \text{eq. 2'}$$

$$\exp(1/(E-M)) \alpha\, SV/EI \qquad \text{eq. 3'}$$

Taking the natural logarithm of both sides of eq. 3', we get $$1/(E-M) \alpha\, \ln(SV/EI) \qquad \text{eq. 4}$$

But by relating to eq. 2', $1/(E-M) \alpha\, \ln(dP/dt_{max})$

Since two quantities that are proportional to the same quantity are proportional to each other, we can write $$\ln(SV/EI) \alpha\, \ln(dP/dt_{max}) \qquad \text{eq. 5}$$

Letting 'B' and 'A' represent the empirical coefficient and constant of linear proportionality respectively, we have, $$\ln(SV/EI) = B(\ln(dP/dt_{max})) + A \qquad \text{eq. 6}$$

The right hand member of eq. 6 contains a quantity, $dP/dt_{max}$, which requires left ventricular catheterization to measure. The left hand side is now easily available with relatively little or no anatomic or physiologic trespass.

In U.S. Pat. No. 7,054,679, data from FIG. 1 was presented according to a schedule of vasoactive infusions shown in Table 1. Incrementally increasing infusion rates of dobutamine were used to increase Contractility. Next incrementally increasing infusion rates of nitroglycerine were used to decrease Preload, and Systemic Vascular Resistance (SVR). Finally, incrementally increasing infusion rates of phenylephrine were used to increase the Systemic Vascular Resistance. At each infusion level, the system was allowed to come to equilibrium. Hemodynamic data, including $dP/dt_{max}$, SV, and EI was recorded during an apneic episode, at Functional Residual Capacity, lasting 60 seconds. This data representing empirical evidence for eq. 6 is presented below in FIG. 1. It is summarized in Table 2.

Figure 1:
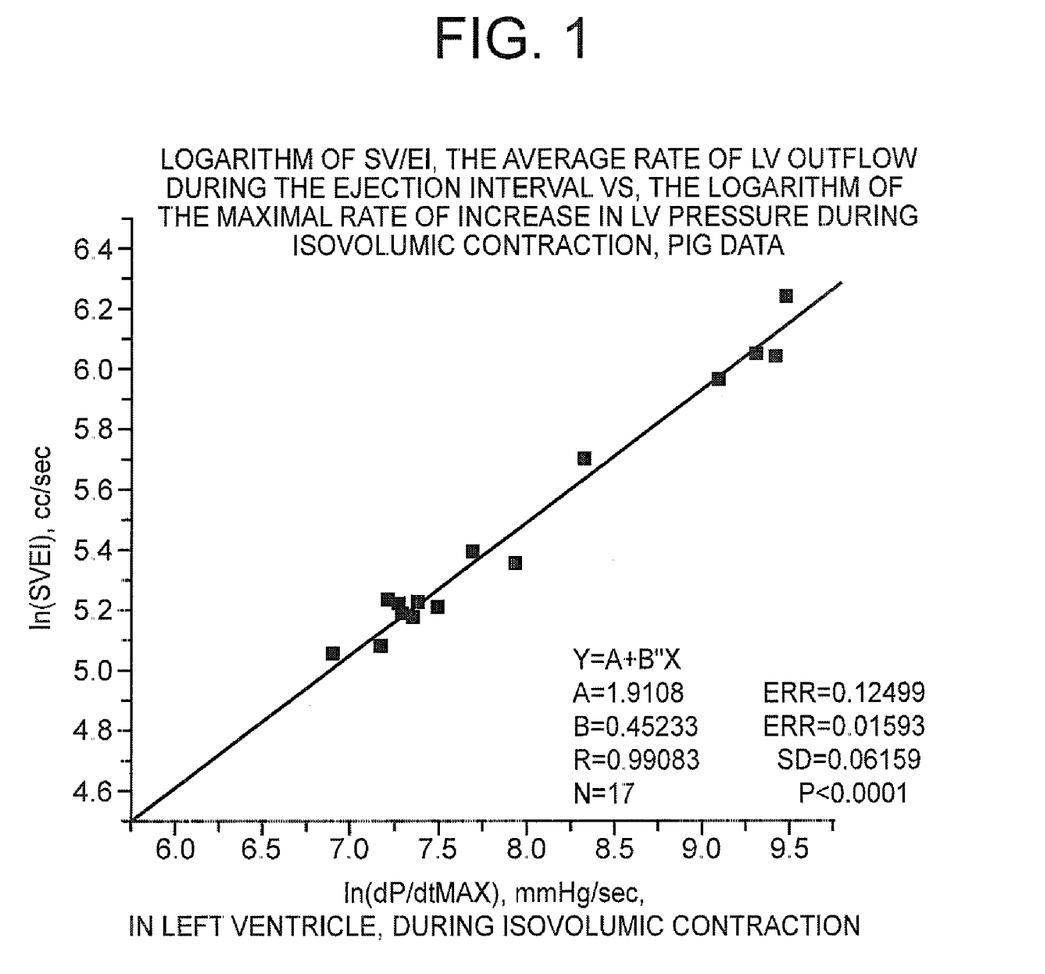
FIG. 1 is a graph illustrating a relation between the logarithm of SV/EI which is the average rate of volume outflow from the Left Ventricle during the systolic ejection interval, and the logarithm of the maximum value of the first derivative of Left Ventricular Pressure with respect to time during systole.

The coefficient B in eq. 6 was measured at 0.452+/−0.016 [ln(cc/sec)/ln(mmHg/sec)]. The constant A in eq. 6 was measured at 1.911+/−0.125 ln(cc/sec). The relation showed a linear correlation coefficient R=0.99, P<0.0001. Eq. 6 applies over 3.5 natural log units with respect to dP/dt max, and nearly 2 natural log units with respect to SV/EI. LVEDP, as a metric of Preload, varied from 1.183 to 19.974 mmHg. Here, Preload spans a range of 2.826 natural log units. SVR, a metric of Afterload, varied from 421 to 12,390 dyne*sec*cm.$^{-5}$. Afterload here, spans a range of 3.382 natural log units. This shows that eq. 6 holds true despite large changes over full physiologic ranges in Preload and Afterload.

TABLE 1

Hemodynamic Steady State Drug Infusion Protocol

| Steady State Number | Drug | Concentration | Infusion Rate, cc/hr |
|---|---|---|---|
| 1 | No drug infusion | | |
| 2 | Dobutamine | 1000 micrograms/cc | 5 |
| 3 | Dobutamine | 1000 micrograms/cc | 10 |

TABLE 1-continued

Hemodynamic Steady State Drug Infusion Protocol

| Steady State Number | Drug | Concentration | Infusion Rate, cc/hr |
|---|---|---|---|
| 4 | Dobutamine | 1000 micrograms/cc | 15 |
| 5 | Dobutamine | 1000 micrograms/cc | 10 |
| 6 | Dobutamine | 1000 micrograms/cc | 30 |
| 7 | No drug infusion | | |
| 8 | Nitroglycerine | 200 micrograms/cc | 3 |
| 9 | Nitroglycerine | 200 micrograms/cc | 10 |
| 10 | Nitroglycerine | 200 micrograms/cc | 100 |
| 11 | Nitroglycerine | 200 micrograms/cc | 200 |
| 12 | Nitroglycerine | 200 micrograms/cc | 500 |
| 13 | No drug infusion | | |
| 14 | Phenylephrine | 40 micrograms/cc | 20 |
| 15 | Phenylephrine | 40 micrograms/cc | 40 |
| 16 | Phenylephrine | 40 micrograms/cc | 80 |
| 17 | Phenylephrine | 40 micrograms/cc | 120 |

TABLE 2

Average Hemodynamic Parameters for Each Hemodynamic Steady State

| Steady State No. | LVEDP mmHg | SVR dyne*sec*cm$^{-5}$ | dP/dt max mmHg/sec | SV cc | EI sec | SV/EI cc/sec |
|---|---|---|---|---|---|---|
| 1 | 9.09666 | 582 | 2707 | 65.95 | 0.3044 | 216.64 |
| 2 | 9.585 | 488 | 4004 | 88.61 | 0.2874 | 308.33 |
| 3 | 1.183 | 464 | 10521 | 61.61 | 0.1400 | 439.96 |
| 4 | 6.895 | 462 | 8521 | 63.2 | 0.1574 | 401.45 |
| 5 | 3.563 | 419 | 11788 | 61.14 | 0.1404 | 435.40 |
| 6 | 5.572 | 357 | 12390 | 71.89 | 0.1355 | 530.57 |
| 7 | 9.238 | 639 | 421 | 33.38 | 0.3237 | 103.13 |
| 8 | 13.63 | 1091 | 989 | 40.93 | 0.2574 | 158.99 |
| 9 | 14.686 | 968 | 1288 | 46.21 | 0.2812 | 164.36 |
| 10 | 12.652 | 809 | 1439 | 49.85 | 0.2732 | 182.46 |
| 11 | 11.89 | 690 | 1545 | 50.09 | 0.2765 | 181.16 |
| 12 | 12.824 | 529 | 1347 | 52.54 | 0.2721 | 193.07 |
| 13 | 14.848 | 837 | 1404 | 49.83 | 0.263 | 189.47 |
| 14 | 15.727 | 982 | 1571 | 50.93 | 0.2673 | 190.56 |
| 15 | 17.907 | 1109 | 1738 | 50.44 | 0.2692 | 187.34 |
| 16 | 18.345 | 1279 | 1783 | 51.77 | 0.2758 | 187.69 |
| 17 | 19.974 | 1079 | 2156 | 62.24 | 0.2756 | 225.83 |

If we allow that $\ln(dP/dt_{max})$ is a useful index of myocardial contractility, then, by eq. 5, $\ln(SV/EI)$, or $(SV/EI)$ will also serve as a useful index of myocardial contractility. The quantity $dP/dt_{max}$ is measured only by placing a catheter into the left ventricle of the heart. This is fraught with peril to the patient. The quantity $\ln(SV/EI)$ has the advantage that it can be easily measured by new and emerging minimally invasive or non-invasive methods on a beat-to-beat basis at low cost and low risk. So we can write $$C=\ln(SV/EI) \quad \text{eq. 7a or}$$

$$C=SV/EI \quad \text{eq. 7b,}$$

where C is myocardial Contractility. The natural log function is useful here precisely because it is monotonically increasing with respect to SV/EI.

Now consider the time-honored equation for the Systemic Vascular Resistance, (SVR), which is generally considered to be a useful approximation to Afterload.

$$SVR = \frac{(MAP - CVP)*80}{CO} \quad \text{eq. 8}$$

where MAP is Mean Arterial Pressure in mmHg, CVP is Central Venous Pressure in mmHg, and CO is Cardiac Output in liters/minute. 80 is a constant used to make the units of SVR come out in dyne*sec*cm-5. Since CVP is ordinarily small compared to MAP, we can write $$SVR=(MAP/CO)*80 \quad \text{eq. 9,}$$

and in fact some manufacturers such as Arrow International with its Hemosonic 100 have already taken this step.

Eqs. 8 and 9 are simply analogous statements of Ohm's Law, which is applied to flowing blood. Yet mathematically, eqs. 8 and 9 are indifferent to whether the cardiac output is continuous and Newtonian, or pulsatile and complex. The resistors in the circuit are not in the venous side, but rather at the end of the arterial circulation in the form of small pre-capillary arteriolar sphincters. This is where the most significant physiologic modulation of the Afterload occurs. It is a function of the tension in the smooth muscle cells that surround the arteriolar sphincters for providing more or less tone according to the ebb and flow of circulating catecholamines.

Eqs. 8 and 9 make sense only if we are talking about blood flow averaged over many consecutive heartbeats as is the case during a single shot thermodilution measurement. It is meaningless on the time scale of less than a single heartbeat or a single systolic ejection interval. And yet, increasingly new technologies are available to measure changes in global Afterload from one heartbeat to the next simply because they routinely allow clinicians to measure variations in Stroke Volume and Ejection Interval from one beat to the next. So with this new wealth of clinical hemodynamic streaming data in hand, it may be time to modify equations 8 and 9 to enable us to talk about how Afterload changes in real physiologic time, and not simply in the interval between one thermodilution CO measurement and the next.

Within the time scale of only one heartbeat, we see that during most of isovolumic contraction, all of left ventricular ejection, and much of isovolumic relaxation, that the mitral valve is firmly closed. So during much of the cardiac cycle, the left ventricle does not even 'see' the CVP. So long as the mitral valve is closed, the CVP has no effect on the Afterload into which the Left ventricle ejects. So an alternative formulation of eq. 9 is $$SVR=\{MAP/[SV/T]\}*k \quad \text{eq. 10,}$$

where SV is given in cm$^3$, and T is the cardiac cycle period in seconds with the constant k adjusted to accommodate the change in units.

It is sensible on this time scale to talk about the resistance to flow during left ventricular ejection. An alternative formulation of eq. 9 then might be $$SVR=MAP/[SV/EI]*k \quad \text{eq. 11}$$

Eqs. 10 and 11 can be considered 'analytical' definitions of SVR inasmuch as they only pertain to a part of the cardiac cycle that excludes ventricular filling. Eq. 10 describes SVR during the portion of the cardiac cycle that includes isovolumic contraction, ejection, isovolumic relaxation, and filling. Eq. 11 describes SVR during the portion of the cardiac cycle that includes ejection only. Inasmuch as eq. 9 describes SVR during many consecutive cardiac cycles, it can be considered a 'gestalt' definition of SVR, in contrast to these alternative, 'analytical' ones.

U.S. Pat. No. 7,054,679, teaches that the Diastolic Filling Interval (DI) as approximated by (T-EI) increases monotonically with respect to the Left Ventricular End-Diastolic Pressure (LVEDP). The monotonically increasing function is not linear, but is rather a Boltzman function of LVEDP with two asymptotes, one at high LVEDP and the other at low LVEDP. Because it is a Boltzman function, a clinician cannot usefully and conveniently reason backwards from a particular DI to a particular LVEDP as the same asymptotic value of DI is assigned to a large range of high LVEDP's. The other asymptotic value of DI is assigned to a large range of low LVEDP's. If DI is very high, you can probably correctly guess that LVEDP is high. On the other hand, if DI is very low, you can probably correctly guess that LVEDP is very low. But based on DI alone, you could not say with any meaningful precision just how high or how low LVEDP really is.

In order to make DI a useful determinant of Preload, the Boltzman relation between it and LVEDP must be linearized or at least adjusted in such a way that the relation is 'one-to-one' and 'onto'. Other things being equal, that is, with a given heart rate, contractility, and SVR, increasing LVEDP will by Starling's Law result in an increase in SV and CO, and then by Ohm's law result in an increase in MAP. That is, MAP=CO*SVR. So we can argue that LVEDP is a monotonically increasing function of MAP, ceteris paribus, given a constant HR, SVR, $\ln(dP/dt_{max})$. LVEDP then is a monotonically increasing function of at least two variables, DI and MAP. These two are necessary but not sufficient.

This necessitates the use of a third variable, and that is contractility or $dP/dt_{max}$. Other parameters being equal, if $dP/dt_{max}$ decreases, then in order to maintain a constant SV and CO, Starling's Law mechanisms must compensate with a raising of the LVEDP. Another way to see this intuitively is to consider that if $dP/d_{tmax}$ suddenly decreases, say due to decreased perfusion and oxygenation of the myocardium, so will the ejection fraction decrease. A decreased ejection fraction will leave a larger residual end-diastolic volume which, other things being equal, will result in a higher LVEDP. By eq. 2, the inverse of (E-M) is linearly proportional to $\ln(dP/dt_{max})$. So it follows that (E-M) is inversely proportional to $\ln(dP/dt_{max})$, that is, $$(E-M) \alpha 1/[\ln(dP/dt_{max})] \qquad \text{eq. 12}$$

Solving eq. 4 for (E-M) we have $$(E-M) \alpha 1/\ln(SV/EI) \qquad \text{eq. 13}$$

This means that wherever we see the quantity (E-M) in U.S. Pat. No. 7,054,679, we can substitute the quantity $1/\ln(SV/EI)$. For instance, U.S. Pat. No. 7,054,679 teaches that $$LVEDP \alpha (DI)(MAP)(E-M) \qquad \text{eq. 14}$$

This is a triple product of three variables each of which has a monotonically increasing relation to LVEDP, given that other parameters are held constant. Note that the triple product is the simplest function of three monotonically increasing variables with respect to LVEDP. In principle, any monotonically increasing function of the three variables in the right hand member of eq. 14 would serve the purpose since it maintains the one-to-one and onto relation. For instance, we could represent DI, MAP and (E-M) as mutually orthogonal Cartesian vectors. In that case, we can write $$LVEDP \alpha [DI^2 + MAP^2 + (E-M)^2]^{1/2} \qquad \text{eq. 15}$$

or the norm of the vector sum of the three vector quantities, which would serve as well. The units of DI and E-M can be in milliseconds, and the units of MAP can be in millimeters of mercury. The invention does NOT consist in the algebraic details of the equation, but rather in the embodiments that utilize or display any useful relation between the three variables in the non-invasive vector space N or N' and a quantity which tracks in a monotonically increasing 'one-to-one', or 'onto' relation, if not in a linear fashion, with the LVEDP or any of the other invasively measured parameters. For example, substituting for (E-M) in eq. 13 using q. 14, we can write $$LVEDP \alpha (DI)(MAP)/\ln(SV/EI) \qquad \text{eq. 16}$$

Observe that eqs. (7a or 7b), (10 or 11), and (15 or 16) combine to yield a three dimensional vector that scales with $[LVEDP, SVR, dP/dt_{max}]$ and is drawn entirely from the new non-invasive vector space N'. We can summarize, for example, as follows, Let N'={T, DI, EI, MAP, SV} be a vector in a non-invasive hemodynamic vector space, where T, DI, EI are in seconds, MAP is in mmHg, and SV is in cc.

Then

| | |
|---|---|
| 1) Heart Rate | HR = 60/T beats/min |
| 2) Cardiac Output | CO = (SV/T) * .06 liters/min |
| 3) Preload | LVEDP = $k_1$ * [(DI)(MAP)/ln(SV/EI)] + $c_1$, mmHg |
| 4) Afterload | SVR = $k_2$*{MAP/[SV/T]} + $c_2$, dyne*(cm*sec$^{-5}$) |
| 5) Contractility | C = ln($k_3$*SV/EI) |

Here, $k_1$, $k_2$ are proportionality coefficients, and $c_1$, $c_2$ proportionality constants. $k_3$ is in units of sec/cc such that the argument of the natural log function is dimensionless. Its value can be arbitrarily set equal to 1 sec/cc. C then, is a dimensionless, monotonically increasing, and clinically useful index of myocardial contractility. A similar constant can be used in the argument of any other log function such as the Preload equation above in line 3. In that case, the units of $k_1$ would be sec$^{-1}$, and the units of $c_2$ would mmHg.

Once {LVEDP, SVR, C} is calculated, it is a simple matter to display it as a vector in a three dimensional Cartesian hemodynamic vector space on a computer display. This informs the clinician on how these physiologically primitive parameters change as a function of time, at a glance. It can be used clinically to titrate the administration of fluid, diuretics, and vasoactive agent therapy, in a real-time, physiologically intelligible and meaningful way.

In analogy with what was taught in U.S. Pat. No. 7,054,679, it is possible to use the information in N' to identify episodes of myocardial ischemia. We need only substitute the term [1/ln(SV/EI)] for [E-M] and make the appropriate changes in the size and the units of the proportionality coefficients and constants.

An early predictor of myocardial ischemia is a decrease in left ventricular compliance, dV/dP in diastole. This decrease in dV/dP precedes the advent of Left Ventricular Wall Motion Abnormalities on 2D echocardiography, which in turn, precedes the advent of ST-segment elevation on EKG as a diagnostic sign of myocardial ischemia. It follows that if clinicians had a running average of dV/dP derived from non-invasive parameters such as N', they would also have an earlier non-invasive diagnostic indication of myocardial ischemia. This could empower clinicians to institute earlier treatment for myocardial ischemia, perioperatively and in the critical care sphere, which would decrease morbidity and mortality.

We can approximate dV/dP by ΔV/ΔP which is just the change in LV volume divided by the change in LV pressure during diastolic filling. Here, $$\Delta V = V_{end\text{-}diastole} - V_{end\text{-}isovolumic\ relaxation}$$ and $$\Delta P = P_{end\text{-}diastole} - P_{end\text{-}isovolumic\ relaxation}$$

But, ΔV=SV, the Stroke Volume, which is a given, in N'. Moreover, if $P_{end\text{-}isovolumic\ relaxation}$ is small compared to $P_{end\text{-}diastole}$ when we can write $$\Delta P = P_{end\text{-}diastole} = LVEDP$$

By eq. 16, ΔP α (DI)(MAP)/ln(SV/EI) and by substitution, $$\Delta V/\Delta P \alpha SV/\{(DI)(MAP)/\ln(SV/EI)\}$$  eq. 17

The right hand member of eq. 17 can be easily calculated on a real-time basis using the data stream contained in N'. There will necessarily be some respiratory variation in that quantity, which can be averaged over a respiratory cycle. But sudden decreases in the numerical value of eq. 17 indicate decreases in myocardial wall compliance and myocardial ischemia. Computer software trends and tracks ΔV/ΔP. The operator is alerted when the myocardial compliance decreases below some pre-determined threshold or fraction of its baseline value.

In another embodiment of the invention, myocardial ischemia, software is implemented to look for a pattern in Preload, Afterload, Contractility and Heart Rate that is the signature of myocardial ischemia. In myocardial ischemia, diastolic function is impaired and LV wall compliance decreases. Physiologic compensation for this results in the heart moving up on the Starling curve, increasing LVEDP. Catacholamine release occurs. Sweating and tachycardia ensue. Heart rate goes up. Systemic Vascular Resistance goes up by way of compensation for the decrease in SV and CO. This results in paleness of appearance and coolness of the skin to the touch since the pre-capillary sphincters that allow blood to flow to the skin constrict, shunting blood away toward vital organs such as the heart, lungs and brain. Contractility decreases to cause decreased stroke volume and cardiac output. So, by looking simultaneously at all of the physiologically primitive hemodynamic parameters, it is possible to see a pattern over a short course of time on the order of one or more minutes, which is the signature of myocardial ischemia. That pattern consists in;

1) Decreased contractility
2) Increased SVR
3) Increased LVEDP
4) Decreased CO
5) Decreased SV A software pattern recognition system can be created to recognize the emergence of such a pattern over a short time course. This would be useful to the clinician in the rapid diagnosis of myocardial ischemia.

Figure 2:
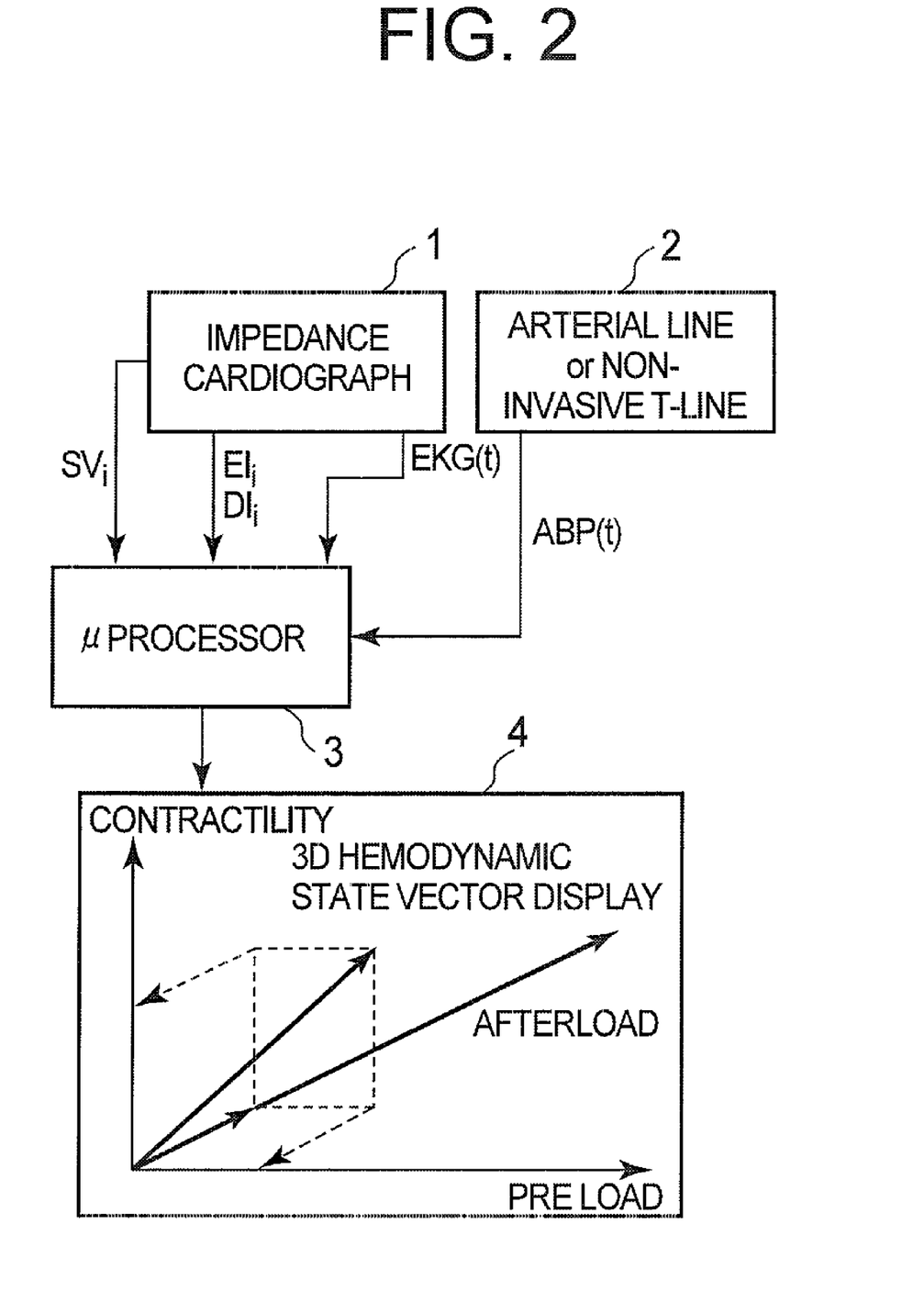
FIG. 2 is a diagram illustrating one preferred embodiment of the current invention using trans-thoracic impedance cardiography.

FIG. 2 shows one preferred embodiment of the invention using trans-thoracic impedance cardiography 1. This technology allows for the non-invasive calculation of the ith Stroke Volume SVi and the ith Ejection Interval (EIi). It can also be used to measure the ith Diastolic Filling interval (DIi). 'i' is the index of consecutive heartbeats. DIi can also be usefully approximated as Ti-EIi, where Ti is the ith cardiac cycle period, which is measured as the time from ith R-wave to the (i+1)th R-wave on EKG. The ith R-wave is the EKG peak just prior to the upstroke in the ABP(t) wave or the maximum value of the second derivative of the ABP(t) curve. The ith EI, by definition, follows the ith R-wave immediately.

Mean Arterial Pressure, (MAP) can be obtained from the indwelling arterial line or non-invasive T-line 2. MAP is calculated in microprocessor 3 by integrating the ABP(t) curve over one cardiac cycle, then dividing by the cardiac period, (Ti). Alternatively, it can be usefully approximated as the diastolic pressure (DP) plus ⅓ of the pulse pressure (SP-DP), where SP is the systolic pressure. Microprocessor 3 uses this streaming data to calculate indices of Preload or LVEDP, Afterload or SVR, and Contractility or $dP/d_{tmax}$. These physiologically primitive parameters are displayed on a computer screen as numbers as well as a vector in three-dimensional Cartesian vector space 4. Display 4 optionally has bar graphs to depict SV and CO, as well as numerical displays for these quantities. It also optionally has a graphical/numerical display of the diastolic compliance of the LV as described in the above algorithm.

In addition, E-M intervals are calculated using EKG(t) and ABP(t) data and SVi, CO, and P, A, C parameters are calculated by microprocessor 3 as a check on the parameters provided by Impedance Cardiography device 1. These parameters are easily calculated using the algorithm taught in U.S. Pat. No. 7,054,679 by microprocessor 3, and calibrated using the ordinary methods used by Impedance Cardiography. These additional parameters would prove useful in the event that artifact or other circumstances made SVi inaccurate or impossible to detect using Impedance Cardiography.

Figure 3:
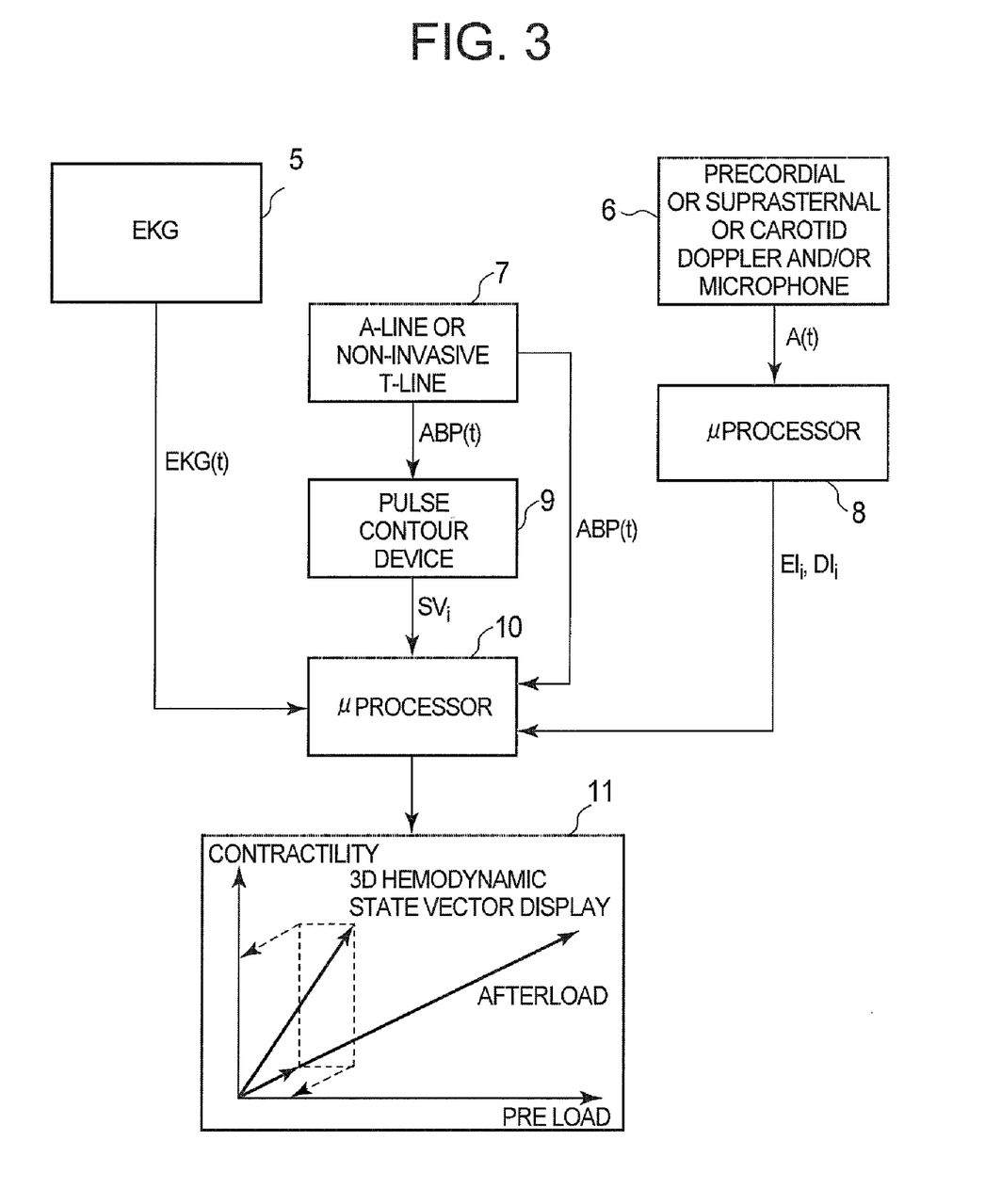
FIG. 3 is a diagram illustrating an embodiment of the current invention using a Pulse Contour Device.

FIG. 3 shows an embodiment of the system using a Pulse Contour Device. At least one version of this device is calibrated using a one-time dose of Lithium ion and an indwelling vascular Lithium electrode measuring the area under a concentration vs. time curve in analogy to thermodilution. The Pulse Contour Device 9 derives SVi from the morphology of the arterial pulse contour ABP(t) obtained from indwelling arterial line or T-line 7. A Precordial or Suprasternal or Carotid Doppler 6 supplies V(t) which is the large arterial blood velocity in the LV, ascending aorta or carotid artery respectively. The V(t) streaming data feeds into a microprocessor 8, which yields EIi and DIi. Alternatively, DIi and EIi are usefully approximated from the amplitude A(t) of the sounds of aortic and mitral valve closure obtained from a precordial stethoscope and/or microphone 6. EKG 5 feeds EKG(t) into microprocessor 10, along with SVi, EIi, DIi, and ABP(t). The microprocessor 10 uses the algorithms described in the above to create {Preload, Afterload, Contractility} which are averaged or continuously averaged as necessary over one or more respiratory cycles, and are displayed as a vector on display screen 11. Display 11 and Display 4 are essentially identically updated.

In addition, E-M intervals are calculated using EKG(t) and ABP(t) data and SVi, CO, and P, A, C parameters are calculated as a check on the parameters provided by Pulse Contour device 9. These parameters can be easily calculated using the algorithm taught in U.S. Pat. No. 7,054,679, by microprocessor 10, and calibrated using the ordinary methods by which Pulse Contour technology is calibrated. This additionally would prove useful in the event that artifact or other circumstances made SVi inaccurate or impossible to detect using Impedance Cardiography.

Figure 4:
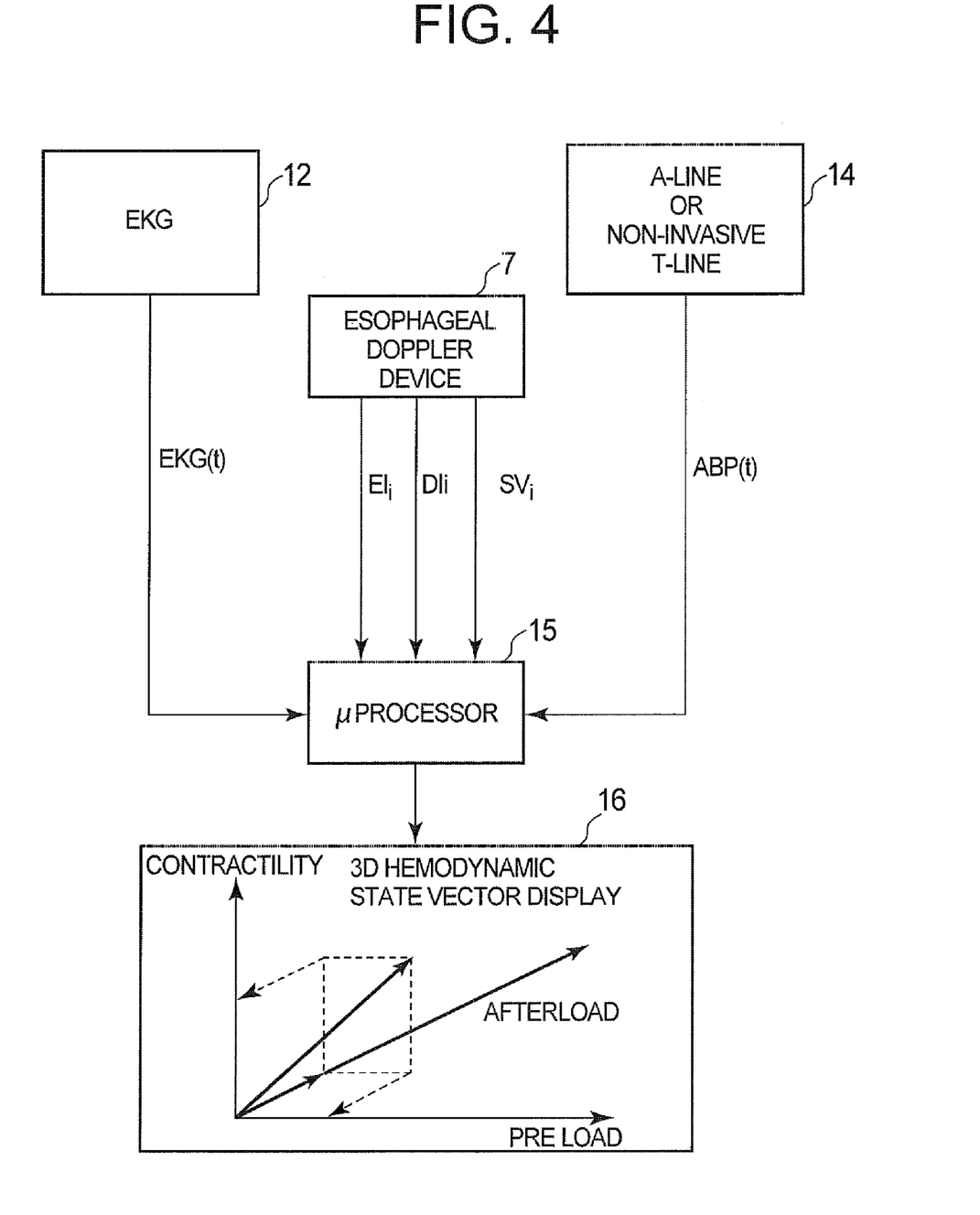
FIG. 4 is a diagram illustrating another embodiment of the current invention using an esophageal Doppler system

In FIG. 4, another embodiment of the invention relies on an esophageal Doppler system such as the Deltex or the Hemosonic 100. This device is used only while the patient is under anesthesia since it is inserted through the mouth into the esophagus. While it is inserted in the esophagus, it is used to create calibration curves which will be useful later. When SVi information is no longer available directly from the esophageal Doppler monitor after it is removed, the calibration curves are used to calculate SVi after the patient emerges from anesthesia, say in the Post-Anesthesia Care Unit. These calibration curves establish the coefficient and constant in the linear relation between [SV/EI] and exp(1/E-M). SVi is simply [SV/EI]i*EIi. This information can be used, in turn to calibrate other hemodynamic parameters such as SVR. E-M is used along with MAP and DI to create a clinically useful index of LVEDP, provided that another complementary means such as a precordial Doppler or precordial Stethoscope is used to measure EIi and DIi after the esophageal Doppler device has been removed. This has been previously taught in U.S. Pat. No. 7,054,679.

While the patient is operated on or under sedation in the intensive care unit (ICU), the Esophageal Doppler device 13 is used to generate SVi and EIi. DIi is approximated from Ti-EIi, the cardiac period minus the Ejection Interval. Microprocessor 15 determines MAPi from ABP(t), obtained from A-line or non-invasive T-line 14. Microprocessor 15 also determines Ti from the interval between consecutive R-waves from EKG 12. E-M intervals are also calculated using data from EKG 12 and A-line or non-invasive T-line 14. Microprocessor 15 determines the {P,A,C} quantities using the algorithms described above or in U.S. Pat. No. 7,054,679. Display 16 is essentially identical to display 11 and display 4 in their functions among all three preferred embodiments of the invention.

Recent work by Gunn 2006 was done using an electromagnetic flow probes to test the accuracy of esophageal Doppler and pulse contour methods used to determine SVi. The authors used an inflatable balloon in the inferior vena cava to create linearly decreasing trains of SVi. They correlated the SVi measured with the electromagnetic flow probe that is considered a 'gold standard' against the Deltex CardioQ esophageal Doppler and the Pulsion PiCCO pulse contour devices. They repeated the measurements with steady state infusions of vasoactive agents dobutamine, norepinephrine and nitroprusside. Each steady state infusion of each agent served to put the dog into a very different part of Hemodynamic Space, in terms of the locus of the {P,A,C} Cartesian vector. Data was collected on 5 different dogs. Remarkably, with each different vasoactive infusion, the calibration coefficient and constant changed significantly. We can conclude that for the Deltex esophageal Doppler and the Pulsion PiCCO, pulse contour methods of generating SVi data depend on an algorithms whose calibration is not isotropic with respect to hemodynamic {P,A,C} space.

By contrast, the algorithm taught by U.S. Pat. No. 7,054,679 generates SVi data whose calibration relations are isotropic and invariant with respect to large swings in Preload, Afterload, and Contractility. The calibration relations once determined, persist through time, well into the peri-operative period. This calibration isotropy and invariance of SVi measurement with respect to large changes in {P,A,C} shows that there exists a role for the algorithm described in U.S. Pat. No. 7,054,679, that can complement and make more robust SVi determinations by esophageal Doppler and pulse contour systems now on the market. These extant systems based upon Lithium ion dilution, thermodilution, and esophageal Doppler are used to initially calibrate the SVi relation in a particular part of {P,A,C} space, per U.S. Pat. No. 7,054,679, or the present invention. These systems are also used to calculate the variation in SVi through time to render useful information regarding {P,A,C}. This is done in a way that does not cause the calibration of the SVi relation to change with large swings in Preload, Afterload, or Contractility.

The quantity SV/EI is a useful measure of myocardial contractility. In the context of a tread mill stress test such as the Bruce Protocol or a dobutamine infusion stress test, it is a useful measure of myocardial contractile organ reserve. It is useful to know how much myocardial contractile reserve a patient has, particularly prior to surgery. This is particularly useful for patients with known cardiac history such as coronary artery disease, prior myocardial infarction or valve disease. The present state-of-the-art entails the use of a cardiac ejection fraction to make this contractility assessment. The ejection fraction is just the stroke volume divided by the end-diastolic volume. It is measured using a radio-nuclide infusion in conjunction with a 3-dimensional imaging gamma ray counter, or using a trans-thoracic 2-dimensional echocardiogram.

One problem with the use of the ejection fraction is that this quantity will vary, for a given level of myocardial contractility, depending on ambient LVEDP and the SVR, which happen to obtain at the time it is measured. As shown in the above, the quantity SV/EI has the advantage that it is invariant over a wide range of LVEDP and SVR, that is, over a wide range of Preload and Afterload. Since there are new non-invasive ways to measure SV/EI, such as with Impedance Cardiography, it is a useful improvement in the state of the art to measure SV/EI at rest and/or under stress conditions as described above, as part of routine pre-anesthetic assessment of the patient.

Intra-operatively and peri-operatively, the SV/EI will vary spontaneously with the patient's need for tissue oxygen perfusion homeostasis. Empirically, there are variations due to positive pressure or spontaneous ventilation with a period equal to the respiratory rate. A running average is determined by averaging a predetermined number of consecutive or adjacent data points, and the same number of data points is continuously taken over the data set to smooth the data line. When these respiratory variations are summed over using a running averaged SV/EI data, a longer period of variation in contractility cycles (i.e. a cyclic change in the running averaged SV/EI data) is revealed on the order of between 10-100 seconds. The variations are an indication of homeostatic processes at work in the auto-regulation of myocardial contractility. When they diminish or disappear, the patient is functioning near the point of myocardial contractile decompensation or in extremis. A measurement of the periodicity of SV/EI changes intra-operatively as seen in the average period of variation, the standard deviation of the period of variation, the amplitude of variation, the standard deviation of the amplitude variation as well as the actual value of SV/EI itself, and they are all useful metrics of contractile function.

While there have been described what are believed to be the preferred embodiments of the present invention, those skilled in the art will recognize that other and further changes and modifications may be made thereto without departing from the spirit of the invention, and it is intended to claim all such changes and modifications as fall within the true scope of the invention.

What is claimed:

1. A method of monitoring cardiac parameters, comprising the steps of:

calibrating a stroke volume as denoted by SV and mean arterial pressure as denoted by MAP in a minimally invasive manner;

non-invasively measuring from a subject a plurality of predetermined non-invasive cardiac parameters including the MAP, the SV, a cardiac period as denoted by T, a diastolic filling interval from the opening to the closing of the mitral valve as denoted by DI and an ejection interval as denoted by EI;

converting the non-invasive cardiac parameters into a plurality of invasive cardiac analogues including preload as denoted by P, afterload as denoted by A and contractility as denoted by C in a monotonically increasing one-to-one and onto manner; and displaying a vector indicating a hemodynamic state.

2. The method of monitoring cardiac parameters according to claim 1 wherein the subject is a human.

3. The method of monitoring cardiac parameters according to claim 1 wherein the subject is an animal.

4. The method of monitoring cardiac parameters according to claim 1 wherein said converting step is performed based upon predetermined conversion equations including $P=k1*[(DI)(MAP)/\ln(SV/EI)]+c1,$ $A=k2*[MAP/(SV/T)]+c2,$ and $C=\ln(k3*SV/EI)$ where k1, k2, k3, c1, c2 and c3 are empirical proportionality constants.

5. The method of monitoring cardiac parameters according to claim 1 further comprising the step of displaying the invasive cardiac analogues in three dimensional coordinate space that is defined by a first axis indicative of the P, a second axis indicative of the A and a third axis indicative of the C.

6. The method of monitoring cardiac parameters according to claim 5 further comprising an additional step of displaying a three dimensional object defining a safe zone indicative of a safe hemodynamic state.

7. The method of monitoring cardiac parameters according to claim 6 wherein the first axis, the second axis, the third axis and the three dimensional object are each displayed with a predetermined color.

8. The method of monitoring cardiac parameters according to claim 1 further comprising an additional step of displaying a vector cross product between the vector and a predetermined vector indicating an amount of physiologic stress.

9. The method of monitoring cardiac parameters according to claim 1 further comprising an additional step of determining a fitness level of the subject based upon the invasive cardiac analogues.

10. The method of monitoring cardiac parameters according to claim 1 further comprising an additional step of determining management of an anesthetic-related procedure of the subject based upon the invasive cardiac analogues.

11. The method of monitoring cardiac parameters according to claim 1 further comprising an additional step of determining an abnormal cardiac condition of the subject based upon the invasive cardiac analogues.

12. The method of monitoring cardiac parameters according to claim 1 further comprising an additional step of transferring the non-invasive cardiac parameters from one location to another location before converting the non-invasive cardiac parameters into the invasive cardiac analogues.

13. The method of monitoring cardiac parameters according to claim 12 further comprising an additional step of evaluating a cardiac condition of the subject based upon the invasive cardiac analogues.

14. The method of monitoring cardiac parameters according to claim 1 wherein $C \propto \ln(SV/EI)$, wherein SV is obtained in a non-invasive manner.

15. A system for monitoring cardiac parameters comprising:

a calibration unit for calibrating a stroke volume as denoted by SV and mean arterial pressure as denoted by MAP in a minimally invasive manner;

a non-invasive cardiac parameter measuring unit connected to said calibration unit for non-invasively measuring from a subject a plurality of predetermined non-invasive cardiac parameters including the SV, the MAP, a cardiac period as denoted by T, a diastolic filling interval from the opening to the closing of the mitral valve as denoted by DI and an ejection interval as denoted by EI;

a conversion unit connected to said non-invasive cardiac parameter measuring unit for converting the non-invasive cardiac parameters into a plurality of invasive cardiac analogues including preload as denoted by P, afterload as denoted by A and contractility as denoted by C in a monotonically increasing one-to-one and onto manner; and a display unit connected to said conversion unit for displaying a vector indicative of a hemodynamic state.

16. The system for monitoring cardiac parameters according to claim 15 wherein said non-invasive cardiac parameter measuring unit measures the predetermined non-invasive cardiac parameters from a human.

17. The system for monitoring cardiac parameters according to claim 15 wherein said non-invasive cardiac parameter measuring unit measures the predetermined non-invasive cardiac parameters from an animal.

18. The system for monitoring cardiac parameters according to claim 15 wherein said non-invasive cardiac parameter measuring unit further comprises a vibration sensing device including at least one of a Doppler ultrasound device, an optical plethysmographic device and a fiber optic device.

19. The system for monitoring cardiac parameters according to claim 15 wherein said conversion unit determines the P, the A and the C based upon predetermined conversion equations including $P=k1*[(DI)(MAP)/\ln(SV/EI)]+c1,$ $A=k2*[MAP/(SV/T)]+c2,$ and $C=\ln(k3*SV/EI)$ where k1, k2, k3, c1, c2 and c3 are empirical proportionality constants.

20. The system for monitoring cardiac parameters according to claim 15 wherein said display unit additionally displays a three dimensional object defining a safe zone indicative of a safe hemodynamic state.

21. The system for monitoring cardiac parameters according to claim 15 wherein said display unit displays the first axis, the second axis, the third axis and the safe zone respectively in a predetermined color.

22. The system for monitoring cardiac parameters according to claim 15 wherein said display unit additionally displays a vector cross product between the vector and a predetermined vector indicative of an amount of physiologic stress.

23. The system for monitoring cardiac parameters according to claim 15 further comprising a determination unit connected to said conversion unit for determining a fitness level of the subject based upon the invasive cardiac analogues.

24. The system for monitoring cardiac parameters according to claim 15 further comprising a determination unit connected to said conversion unit for determining management of an anesthetic-related procedure of the subject based upon the invasive cardiac analogues.

25. The system for monitoring cardiac parameters according to claim 15 further comprising a determination unit connected to said conversion unit for determining an abnormal cardiac condition of the subject based upon the invasive cardiac analogues.

26. The system for monitoring cardiac parameters according to claim 15 further comprising a data communication unit connected to said non-invasive cardiac parameter measuring unit at one location for transferring the non-invasive cardiac parameters to said conversion unit at another location before converting the non-invasive cardiac parameters into the invasive cardiac analogues.

27. The system for monitoring cardiac parameters according to claim 15 wherein said data communication unit transfers the non-invasive cardiac parameters to said conversion unit via the Internet.

28. The system for monitoring cardiac parameters according to claim 15 wherein said data communication unit transfers the non-invasive cardiac parameters to said conversion unit via telecommunication.

29. The system for monitoring cardiac parameters according to claim 15 wherein said non-invasive cardiac parameter measuring unit is portable.

30. The system for monitoring cardiac parameters according to claim 15 wherein said conversion unit is retrofitted to an existing one of said non-invasive cardiac parameter measuring unit.

31. The system for monitoring cardiac parameters according to claim 15 wherein $C \propto \ln(SV/EI)$, wherein SV is obtained in a non-invasive manner.

32. A method of monitoring cardiac parameters, comprising the steps of:
measuring in a substantially non-invasive manner from a subject a plurality of predetermined non-invasive cardiac parameters including a stroke volume as denoted by SV, mean arterial pressure as denoted by MAP, a cardiac period as denoted by T, a diastolic filling interval from the opening to the closing of the mitral valve as denoted by DI and an ejection interval as denoted by EI;
converting the non-invasive cardiac parameters into a plurality of invasive cardiac analogues including preload as denoted by P, afterload as denoted by A and contractility as denoted by C in a monotonically increasing one-to-one and onto manner; and
displaying a vector indicating a hemodynamic state.

33. The method of monitoring cardiac parameters according to claim 32 wherein $C \propto \ln(SV/EI)$, wherein SV is obtained in a non-invasive manner.

34. A system for monitoring cardiac parameters comprising:
a non-invasive cardiac parameter measuring unit for measuring in a substantially non-invasive manner from a subject a plurality of predetermined non-invasive cardiac parameters including a stroke volume as denoted by SV, mean arterial pressure as denoted by MAP, a cardiac period as denoted by T, a diastolic filling interval from the opening to the closing of the mitral valve as denoted by DI and an ejection interval as denoted by EI;
a conversion unit connected to said non-invasive cardiac parameter measuring unit for converting the non-invasive cardiac parameters into a plurality of invasive cardiac analogues including preload as denoted by P, afterload as denoted by A and contractility as denoted by C based in a monotonically increasing one-to-one and onto manner; and
a display unit connected to said conversion unit for displaying a vector indicative of a hemodynamic state.

35. The system for monitoring cardiac parameters according to claim 34 wherein $C \propto \ln(SV/EI)$, wherein SV is obtained in a non-invasive manner.

36. A method of evaluating a patient based upon non-invasively measured parameters of myocardial contractility, comprising the steps of:
measuring in a substantially non-invasive manner from the patient a plurality of predetermined non-invasive cardiac parameters including a stroke volume as denoted by SV and an ejection interval as denoted by EI at rest and under duress; and
equating one of SV/EI and ln(SV/EI) to the myocardial contractility.

37. The method of evaluating a patient based upon non-invasively measured parameters according to claim 36 wherein said equating step equates the measured SV/EI to a level of myocardial contractile reserve and further comprising an additional step of making pre-anesthetic assessment based upon the level of the myocardial contractile reserve.

38. The method of evaluating a patient based upon non-invasively measured parameters according to claim 37 wherein the pre-anesthetic assessment is made over a wide range Systemic Vascular Resistance (SVR) and Left Ventricular End-Diastolic Pressure (LVEDP).

39. The method of evaluating a patient based upon non-invasively measured parameters according to claim 36 wherein said equating step equates the measured SV/EI to a level of myocardial contractility and further comprising an additional step of making intra-anesthetic assessment based upon the myocardial contractility.

40. The method of evaluating a patient based upon non-invasively measured parameters according to claim 36 wherein said equating step equates the measured SV/EI to a level of myocardial contractility and further comprising an additional step of making peri-anesthetic assessment based upon the myocardial contractility.

41. A system for making pre-anesthetic assessment of a patient based upon measure of myocardial contractility, comprising:
a cardiac parameter measuring unit for measuring in a substantially non-invasive manner from the patient a plurality of predetermined non-invasive cardiac parameters including a stroke volume as denoted by SV and an ejection interval as denoted by EI; and
a determination unit connected to said non-invasive cardiac parameter measuring unit for equating one of SV/EI and ln(SV/EI) to myocardial contractility.

42. The system for making pre-anesthetic assessment of a patient according to claim 41 wherein said determination unit equates the measured SV/EI to a level of myocardial contractile reserve and makes pre-anesthetic assessment based upon the level of the myocardial contractile reserve.

43. The system for making pre-anesthetic assessment of a patient according to claim 42 wherein said determination unit makes the pre-anesthetic assessment over a wide range Systemic Vascular Resistance (SVR) and Left Ventricular End-Diastolic Pressure (LVEDP).

44. The system for making pre-anesthetic assessment of a patient according to claim 41 wherein said determination unit equates the measured SV/EI to a level of the myocardial contractility and makes intra-anesthetic assessment based upon the level of the myocardial contractility.

45. The system for making pre-anesthetic assessment of a patient according to claim 41 wherein said determination unit equates the measured SV/EI to a level of the myocardial contractility and makes peri-anesthetic assessment based upon the level of the myocardial contractility.

46. A method of detecting myocardial ischemia in a patient based upon non-invasively measured parameters, comprising the steps of:
- calibrating a stroke volume as denoted by SV and mean arterial pressure as denoted by MAP in a minimally invasive manner for the patient;
- non-invasively measuring from the patient a plurality of predetermined non-invasive cardiac parameters including the MAP, the SV, a cardiac period as denoted by T, a diastolic filling interval from the opening to the closing of the mitral valve as denoted by DI and an ejection interval as denoted by EI;
- approximating the rate of change in volume with respect to the rate of change in pressure in the left ventricle (dV/dP) by the change in LV volume divided by the change in LV pressure during diastolic filling ($\Delta V/\Delta P$); and
- evaluating the $\Delta V/\Delta P$ by the non-invasively measured cardiac parameters; and
- detecting ischemia in the patient based upon the evaluated $\Delta V/\Delta P$.

47. The method of detecting myocardial ischemia according to claim 46 wherein said evaluating step utilizes a relation, $\Delta V/\Delta P \Psi SV/\{(DI)(MAP)/\ln(SV/EI)\}$.

48. The method of detecting myocardial ischemia according to claim 46 wherein said detecting step includes any number of signs in decreased contractility, increased SVR, increased LVEDP, decreased CO and decreased SV, which are derived from the non-invasively measured cardiac parameters.

49. A system for detecting myocardial ischemia in a patient based upon non-invasively measured parameters, comprising:
- a calibration unit for calibrating a stroke volume as denoted by SV and mean arterial pressure as denoted by MAP in a minimally invasive manner for the patient;
- a non-invasively measuring unit connected to said calibration unit for non-invasively measuring from the patient a plurality of predetermined non-invasive cardiac parameters including the MAP, the SV, a cardiac period as denoted by T, a diastolic filling interval from the opening to the closing of the mitral valve as denoted by DI and an ejection interval as denoted by EI; and
- a determination unit connected to said non-invasively measuring unit for approximating the rate of change in volume with respect to the rate of change in pressure in the left ventricle (dV/dP) by the change in LV volume divided by the change in LV pressure during diastolic filling ($\Delta V/\Delta P$) to evaluating the $\Delta V/\Delta P$ by the non-invasively measured cardiac parameters, said determination unit detecting ischemia in the patient based upon the evaluated $\Delta V/\Delta P$.

50. The system for detecting myocardial ischemia according to claim 49 wherein said determination unit evaluates $\Delta V/\Delta P$ based upon $SV/\{(DI)(MAP)/\ln(SV/EI)\}$.

51. The method of detecting myocardial ischemia according to claim 49 wherein said determination unit uses any number of signs in decreased contractility, increased SVR, increased LVEDP, decreased CO and decreased SV, which are derived from the non-invasively measured cardiac parameters.

52. A method of quantifying a subject's ability to effect perfusion homeostasis through the physiologic modulation of myocardial contractility, comprising of the steps of:
- measuring beat-to-beat SV/EI data over time in a substantially non-invasive manner;
- obtaining a running average of the beat-to-beat SV/EI data, where the number of beats in the running average equals the number of beats in one respiratory cycle or at least two consecutive respiratory cycles;
- determining variations in the SV/EI data with respect to the running averaged SV/EI data;
- determining an average of the variations and a standard deviation of the variations to generate a contractile function metric; and
- determining based upon the contractile function metric as to whether or not the subject experiences myocardial contractile decompensation.

53. The method of quantifying a subject's ability to effect perfusion homeostasis according to claim 52 wherein the variations in the SV/EI data is a time period of each of the contractility cycles.

54. The method of quantifying a subject's ability to effect perfusion homeostasis according to claim 53 wherein the contractility cycle is in the order of between 10 and 100 seconds.

55. The method of quantifying a subject's ability to effect perfusion homeostasis according to claim 52 wherein the variations in the SV/EI data is an amplitude of each of the contractility cycles.

56. A system for quantifying a subject's ability to effect perfusion homeostasis through the physiologic modulation of myocardial contractility, comprising:
- a measuring unit for measuring beat-to-beat SV/EI data over time in a substantially non-invasive manner;
- a determination unit connected to said measuring unit obtaining a running average of the beat-to-beat SV/EI data, where the number of beats in the running average equals the number of beats in one respiratory cycle or at least two consecutive respiratory cycles, said determination unit determining variations in the SV/EI data with respect to the running averaged SV/EI data and an average of the variations and a standard deviation of the variations to generate a contractile function metric; and
- a display unit connected to said determination unit for displaying the contractile function metric for determining whether or not the subject experiences myocardial contractile decompensation.

57. The system for quantifying a subject's ability to effect perfusion homeostasis according to claim 56 wherein the variations in the SV/EI data is a time period of each of the contractility cycles.

58. The system for quantifying a subject's ability to effect perfusion homeostasis according to claim 57 wherein the contractility cycle is in the order of between 10 and 100 seconds.

59. The system for quantifying a subject's ability to effect perfusion homeostasis according to claim 56 wherein the variations in the SV/EI data is an amplitude of each of the contractility cycles.

60. A method of monitoring cardiac parameters, comprising the steps of:
- calibrating a stroke volume as denoted by SV and mean arterial pressure as denoted by MAP in a minimally invasive manner;
- non-invasively measuring from a subject a plurality of predetermined non-invasive cardiac parameters including the MAP, the SV, a cardiac period as denoted by T, a diastolic filling interval from the opening to the closing of the mitral valve as denoted by DI and an ejection interval as denoted by EI;
- converting the non-invasive cardiac parameters into a plurality of invasive cardiac analogues including preload as denoted by P, afterload as denoted by A and contractility as denoted by C in a monotonically increasing one-toone and onto manner, $C \propto \ln(SV/EI)$, wherein SV is obtained in a non-invasive manner; and displaying a vector indicating a hemodynamic state.

61. A system for monitoring cardiac parameters comprising:

a calibration unit for calibrating a stroke volume as denoted by SV and mean arterial pressure as denoted by MAP in a minimally invasive manner;

a non-invasive cardiac parameter measuring unit connected to said calibration unit for non-invasively measuring from a subject a plurality of predetermined non-invasive cardiac parameters including the SV, the MAP, a cardiac period as denoted by T, a diastolic filling interval from the opening to the closing of the mitral valve as denoted by DI and an ejection interval as denoted by EI;

a conversion unit connected to said non-invasive cardiac parameter measuring unit for converting the non-invasive cardiac parameters into a plurality of invasive cardiac analogues including preload as denoted by P, afterload as denoted by A and contractility as denoted by C in a monotonically increasing one-to-one and onto manner, $C \propto \ln(SV/EI)$, wherein SV is obtained in a non-invasive manner; and a display unit connected to said conversion unit for displaying a vector indicative of a hemodynamic state.

* * * * *